(12) United States Patent
Gooden et al.

(10) Patent No.: US 11,207,445 B2
(45) Date of Patent: Dec. 28, 2021

(54) ALLOGRAFT BONE PUTTY AND METHODS OF MAKING THE SAME

(71) Applicant: Community Blood Center, Dayton, OH (US)

(72) Inventors: Felicia C. T. Gooden, Beavercreek, OH (US); Robert D. Hoskins, Springboro, OH (US); Shawn A. Hunter, Springboro, OH (US)

(73) Assignee: Community Blood Center, Dayton, OH (US)

(*) Notice: Subject to any disclaimer, the term of this patent is extended or adjusted under 35 U.S.C. 154(b) by 81 days.

(21) Appl. No.: 16/506,347

(22) Filed: Jul. 9, 2019

(65) Prior Publication Data

US 2021/0008250 A1   Jan. 14, 2021

(51) Int. Cl.
  *A61L 27/36* (2006.01)
  *A61L 27/22* (2006.01)
  *A61K 9/00* (2006.01)

(52) U.S. Cl.
  CPC ........ *A61L 27/3608* (2013.01); *A61K 9/0024* (2013.01); *A61L 27/222* (2013.01); *A61L 27/3641* (2013.01); *A61L 27/3683* (2013.01); *A61L 2430/02* (2013.01)

(58) Field of Classification Search
  CPC .......... A61P 19/00; A61P 19/08; A61P 43/00; A61P 9/00; A61K 38/1875; A61K 35/32; A61K 2300/00; A61K 9/0024; A61K 38/18; A61K 35/28; A61K 38/39; A61K 47/22; A61K 31/22; A61K 31/366; A61K 31/40; A61K 31/47; A61K 31/505; A61K 31/00; A61K 38/1825; A61K 38/1841; A61K 38/1866; A61K 38/4886; A61K 47/50; A61K 6/884; A61K 9/5078; A61K 31/405; A61K 31/44; A61K 33/42; A61K 35/35; A61K 31/4418; A61K 31/724; A61K 38/54; A61K 47/42; A61K 6/08; A61L 2430/02; A61L 27/3608; A61L 27/3683; A61L 27/365; A61L 31/048; A61L 24/0005; A61L 27/222; A61L 27/3604; A61L 27/3691; A61L 27/56; A61L 2300/30; A61L 2300/606; A61L 2400/06; A61L 27/20; A61L 27/227; A61L 27/28; A61L 27/3687; A61L 27/52; A61L 27/26; A61L 27/3695; A61L 27/3847; A61L 2300/404; A61L 2300/406; A61L 2300/414; A61L 2300/428; A61L 2400/16; A61L 24/0031; A61L 24/0094; A61L 27/3645; A61L 27/446; A61L 27/46; A61L 27/48; A61L 27/507; A61L 27/54; A61L 31/14; A61L 27/025; A61L 27/10

See application file for complete search history.

(56) References Cited

U.S. PATENT DOCUMENTS

| | | | |
|---|---|---|---|
| 5,073,373 A | 12/1991 | O'Leary et al. | |
| 6,309,659 B1 | 10/2001 | Clokie | |
| 6,576,249 B1 | 6/2003 | Gendler et al. | |
| 6,652,887 B1 | 11/2003 | Richelsoph et al. | |
| 7,498,041 B2 | 3/2009 | Masinaei et al. | |
| 7,785,634 B2 | 8/2010 | Borden | |
| 7,824,702 B2* | 11/2010 | Wironen | B01F 11/0082 424/423 |
| 7,892,577 B2 | 2/2011 | Borden | |
| 9,005,646 B2 | 4/2015 | Masinaei et al. | |
| 9,138,508 B2* | 9/2015 | Borden | A61F 2/07 |
| 9,408,875 B2 | 8/2016 | Masinaei et al. | |
| 2002/0192263 A1* | 12/2002 | Merboth | C08L 5/08 424/426 |
| 2003/0044445 A1* | 3/2003 | Kay | A61L 27/365 424/423 |

FOREIGN PATENT DOCUMENTS

CN    105903003    *  8/2016   .......... A61K 31/194

OTHER PUBLICATIONS

CN105903003 abstract (Year: 2016).*
CN105903003 machine translation (Year: 2016).*
Bayat et al. "Bone Reconstruction following Application of Bone Matrix Gelatin to Alveolar Defects: A Randomized Clinical Trial" International Journal of Organ Transplantation Medicine 2015; vol. 6 (4), 6 pgs.
Li et al. "Demineralized bone matrix gelatin as scaffold for osteochondral tissue engineering" Elsevier, Biomaterials 27 ((2006) 2426-2433, 8 pgs.
Min et al. "MicroRNAs associated with osteoarthritis differently expressed in bone matrix gelatin (BMG) rat model" Int J Clin Exp Med 2015;8(1):1009-1017, 9 pgs.

(Continued)

*Primary Examiner* — Audrea B Coniglio
(74) *Attorney, Agent, or Firm* — Dinsmore & Shohl LLP

(57) ABSTRACT

A method of preparing a reconstitutable implantable bone putty includes combining a bone matrix derived from human bone and gelatin particulates derived from human tissue at a concentration of the bone matrix by dry weight of 20 to 60 percent to form the reconstitutable implantable bone putty. Preparing the gelatin particulates includes supplying a gelatin precursor of bone or soft tissue from a human, treating the gelatin precursor with phosphoric acid to generate a gelatin-acid mixture, neutralizing the gelatin-acid mixture with an alkali to a pH between 6 and 8 to allow a gelatin-rich solution and a waste solution to separate, removing residual salts from the gelatin-rich solution to obtain purified gelatin, drying the purified gelatin, and reducing the purified gelatin to particulates having a largest dimension less than 300 μm. A method of preparing an implantable bone putty includes adding a reconstitution media to the reconstitutable implantable bone putty.

15 Claims, 3 Drawing Sheets

(56) References Cited

OTHER PUBLICATIONS

Shahoon et al. "Comparison of the Human Bone Matrix Gelatin (HBMG) with Autogenous Bone Graft in Reconstruction of the Parietal Bone Defects in Rat: A Histological and Radiographic Study" Journal of Dental Research, Dental Clinics, Dental Prospects, J Dent Res Dent Clin Dent Prospect 2009; 3(2):37-45, 9 pgs.

Urist et al. "Bone Morphogenesis in Implants of Insoluble Bone Gelatin" Proc. Nat. Acad. Sci. USA, vol. 70, No. 12, Part I, pp. 3511-3515, Dec. 1973, 5 pgs.

Wang "Cartilage Tissue Engineering With Demineralized Bone Matrix Gelatin and Fibrin Glue Hybrid Scaffold: An In Vitro Study" Article in Artificial Orangs, Feb. 2010, 7 pgs.

Yan et al. "Bonding of chemically treated titanium implants to bone" Chemically Treated Ti Implants Bonded to Bone, Jul. 8, 1996, 9 pgs.

Nie et al. "In vitro corrosion, cytotoxicity and hemocompatibility of bulk nanocrystalline pure iron" Article in Biomedical Materials, Nov. 2010, 12 pgs.

* cited by examiner

ALLOGRAFT BONE PUTTY AND METHODS OF MAKING THE SAME

TECHNICAL FIELD

The present specification generally relates to implantable bone putty and methods of making the same and, more specifically, allograft bone putty and methods of making the same.

BACKGROUND

Musculoskeletal (spine, trauma, orthopedics/sports medicine) and dental applications commonly call for the use of bone grafts in order to supplement the recipient's healing process. In these applications, surgeons often have difficulty implanting bone grafts into the site for repair without loss of the product or lengthy healing times. Bone putties have been developed which allow molding and packing of the bone graft to conform to any shape or size necessary and to provide pathways for patient bone growth. Many different bone putties are available on the market and are formed from a carrier or binder and an osteoinductive material to facilitate bone healing by recruiting immature cells to the implant site and stimulating cells to an osteogenic phenotype. Many currently available bone putties are fully synthetic or semi-synthetic. Semi-synthetic bone putties use either an allograft or xenograft derived carrier combined with synthetic particulate such as bioglass, tricalcium phosphate, or hydroxyapatite particles; or use a reverse phase medium (RPM) carrier composed of copolymers in which allograft particulate is suspended. In many circumstances a fully allograft-based solution is desirable. However, current allograft-based bone putties either contain viable cells requiring storage in cold conditions and/or are produced using complex, time-consuming, and expensive processes. Accordingly, a need exists for methods of producing a fully allograft-based bone putty which is free of complex extractions or extended chemical treatments and does not require cold storage.

SUMMARY

In accordance with embodiments of the present disclosure, a method of preparing a reconstitutable implantable bone putty is provided. The method includes supplying a bone matrix derived from human bone, preparing gelatin particulates derived from human tissue, and combining the bone matrix and the gelatin particulates at a concentration of the bone matrix by dry weight of 20 to 60 percent to form the reconstitutable implantable bone putty. Preparing the gelatin particulates includes supplying a gelatin precursor comprising bone or soft tissue from a human and treating the gelatin precursor with phosphoric acid to generate a gelatin-acid mixture. Treating the gelatin precursor with phosphoric acid includes agitation of the gelatin precursor and phosphoric acid at a temperature less than 30° C. prior to agitation at a temperature in excess of 50° C. Preparing the gelatin particulates also includes neutralizing the gelatin-acid mixture with an alkali to a pH between 6 and 8, thereby allowing a gelatin-rich solution and a waste solution to separate. The alkali is introduced to the gelatin-acid mixture at a controlled rate and position. Additionally, preparing the gelatin particulates includes removing residual salts from the gelatin-rich solution to obtain purified gelatin, drying the purified gelatin, and reducing the purified gelatin to particulates having a largest dimension less than 300 micrometers (μm) to generate the gelatin particulates.

In accordance with further embodiments of the present disclosure, a method of preparing an implantable bone putty is provided. The method includes preparing a reconstitutable implantable bone putty and adding a reconstitution media to the reconstitutable implantable bone putty. The reconstitution media may be selected from water, saline, blood, plasma, interstitial fluid, fat, cellular medium, or amniotic fluid. Preparing the reconstitutable implantable bone putty includes supplying a bone matrix derived from human bone, preparing gelatin particulates derived from human tissue, and combining the bone matrix and the gelatin particulates at a concentration of the bone matrix by dry weight of 20 to 60 percent to form the reconstitutable implantable bone putty. Preparing the gelatin particulates includes supplying a gelatin precursor comprising bone or soft tissue from a human and treating the gelatin precursor with phosphoric acid to generate a gelatin-acid mixture. Treating the gelatin precursor with phosphoric acid includes agitation of the gelatin precursor and phosphoric acid at a temperature less than 30° C. prior to agitation at a temperature in excess of 50° C. Preparing the gelatin particulates also includes neutralizing the gelatin-acid mixture with an alkali to a pH between 6 and 8, thereby allowing a gelatin-rich solution and a waste solution to separate. The alkali is introduced to the gelatin-acid mixture at a controlled rate and position. Additionally, preparing the gelatin particulates includes removing residual salts from the gelatin-rich solution to obtain purified gelatin, drying the purified gelatin, and reducing the purified gelatin to particulates having a largest dimension less than 300 μm to generate the gelatin particulates.

In accordance with yet further embodiments of the present disclosure, a reconstitutable implantable bone putty is provided. The reconstitutable implantable bone putty is formed from a bone matrix derived from human bone and gelatin derived from human tissue. The bone matrix is present in the bone putty at a concentration by dry weight of 20 to 60 percent. Further, the gelatin is provided in a dried form consisting of grains sized to less than 300 μm.

Additional features and advantages of the technology disclosed in this disclosure will be set forth in the detailed description which follows, and in part will be readily apparent to those skilled in the art from the description or recognized by practicing the technology as described in this disclosure, including the detailed description which follows, the claims, as well as the appended drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
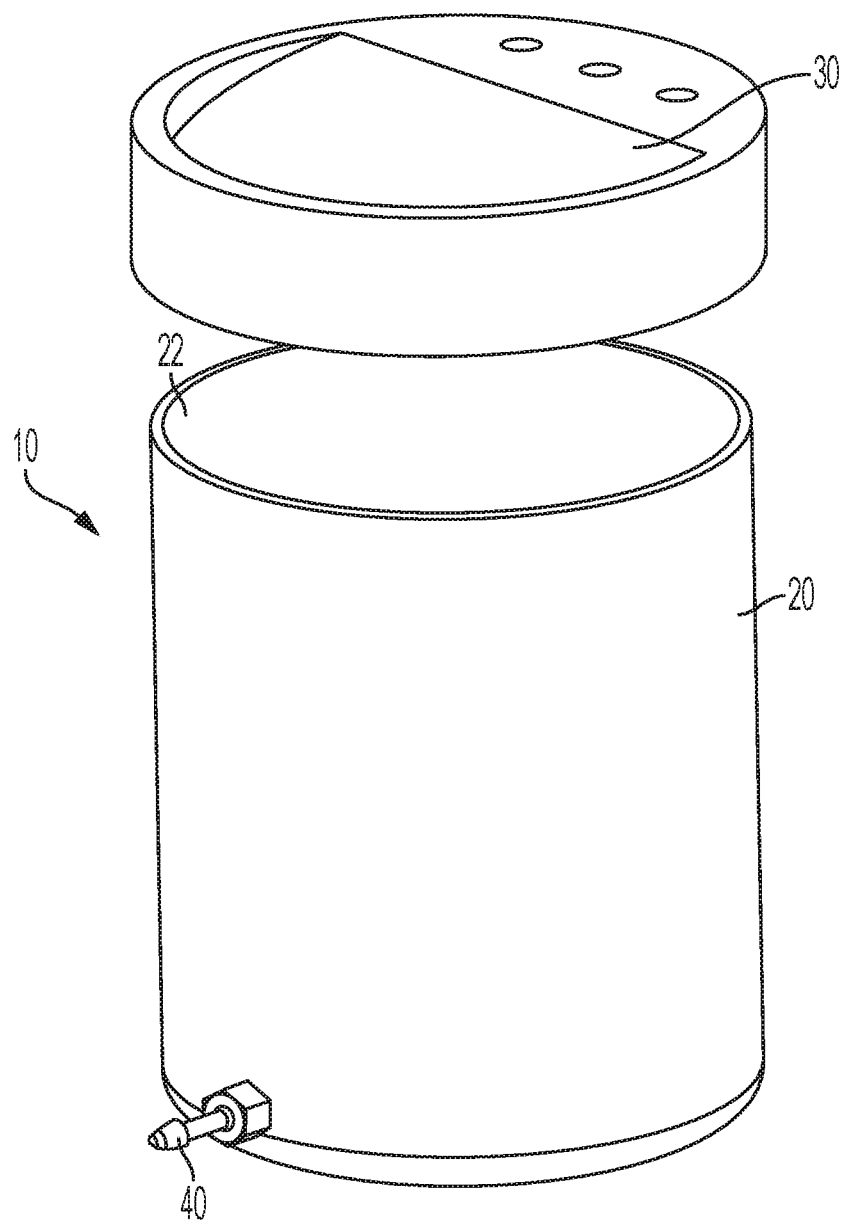
FIG. 1 depicts a customized reaction vessel including a reaction chamber and a distribution lid, according to one or more embodiments shown and described herein.

Reference will now be made in detail to various embodiments of a reconstitutable implantable bone putty and methods of preparing the same. In general, the reconstitutable implantable bone putty comprises a bone matrix derived from human bone and gelatin derived from human tissue, thereby forming a fully allograft-derived bone putty.

Methods of preparing the reconstitutable implantable bone putty comprise supplying a bone matrix derived from human bone, preparing gelatin particulates derived from human tissue, and combining the bone matrix and the gelatin particulates at a concentration of the bone matrix by dry weight of 20 to 60 percent to form the reconstitutable implantable bone putty. Generally, preparing the gelatin particulates comprises supplying a gelatin precursor comprising bone or soft tissue from a human, treating the gelatin precursor with phosphoric acid to generate a gelatin-acid mixture, neutralizing the gelatin-acid mixture with an alkali to a pH between 6 and 8, thereby allowing a gelatin-rich solution and a waste solution to separate, removing residual salts from the gelatin-rich solution to obtain purified gelatin, drying the purified gelatin, and reducing the purified gelatin to particulates having a largest dimension less than 300 µm to generate the gelatin particulates. Treating the gelatin precursor with phosphoric acid comprises agitation of the gelatin precursor and phosphoric acid at a temperature less than 30° C. prior to a second agitation at a temperature in excess of 50° C. Having described the general method of preparing the reconstitutable implantable bone putty, further detail will be provided throughout the present disclosure.

In various embodiments, the bone matrix is formed from mineralized bone matrix, demineralized bone matrix (DBM), or a combination of both. The source of the bone for preparation of the bone matrix may include cortical bone, cancellous bone, or a combination of both. Demineralization exposes bone morphogenic proteins (BMPs) and other biologically pertinent growth factors in the donor bone to facilitate faster bone healing and remodeling in a recipient. Demineralized bone provides the osteoinductive property while mineralized bone may provide an osteoconductive property because it takes much longer to be remodeled and incorporated into the recipient. Cancellous bone provides a greater surface area to volume ratio and lower density in comparison to cortical bone which provides an overall better platform for osteoinduction if demineralized. However, cortical bone is may be more readily available for use than cancellous due to the relative abundance of cortical bone in the skeleton and the high market demand for cancellous bone in grafts. As such, the reconstitutable implantable bone putty being capable of utilizing cortical bone, cancellous bone, or a combination of both allows for increased flexibility in the production process.

In one or more embodiments, the bone matrix is provided as particulates sized to less than 800 micrometers (µm). In various further embodiments, the bone matrix is provided as particulates sized in the range of 100 to 780 µm, 125 to 740 µm, or 125 to 710 µm. The particulates may be separated by size using a vibratory shaker and a series of sieves sized to 125 µm, 200 µm, and 710 µm, for example. Preparation of the bone matrix using too small a particle may create dryness in the reconstitutable implantable bone putty and preparation of the bone matrix using too large a particle may create overly moist reconstitutable implantable bone putty, holding all other production variables constant.

As previously indicated, the gelatin particulates are derived from human tissue. In various embodiments, the human tissue comprises bone, soft tissue, or both. Examples of soft tissues include tendons, skin, fascia, and amniotic membranes. The human tissue provides the gelatin precursor which is converted into the gelatin particulates in accordance with methods described in the present disclosure.

In various embodiments, the gelatin particulates are derived from mineralized bone matrix, demineralized bone matrix (DBM), or a combination of both as provided by the gelatin precursor. In one or more embodiments, the bone supplied as the gelatin precursor has a concentration of $Ca^{2+}$ of less than 8% by weight. In further embodiments, the bone supplied as the gelatin precursor has a concentration of $Ca^{2+}$ of less than 6% by weight, 4% by weight, 2% by weight, or 1% by weight. It will be appreciated by one skilled in the art that Calcium is measured by inductively coupled plasma atomic emission spectroscopy (ICP-AES) in milligrams per kilograms (mg/kg) units and divided by 10,000 to obtain the percentage value. Minimizing the concentration of $Ca^{2+}$ within the gelatin precursor minimizes generation of calcium phosphates during processing of the gelatin precursor into the gelatin particulates. Calcium phosphates are desirably avoided as trisodium phosphate, which has toxicity to patients, cannot be easily separated from the calcium phosphates remaining in the gelatin particulates.

The source of the bone for the gelatin precursor may include cortical bone, cancellous bone, or a combination of both. In one or more specific embodiments, the gelatin particulates are derived from demineralized human cortical bone supplied as the gelatin precursor.

Having briefly described the gelatin particulates, methods of preparing the gelatin particulates will be described in further detail.

Initially the gelatin precursor is treated with phosphoric acid to generate a gelatin-acid mixture. The addition of phosphoric acid to the gelatin precursor results in denaturation of a collagen matrix within the gelatin precursor. In one or more embodiments, the phosphoric acid is orthophosphoric acid. It will be appreciated that selection of acid to generate the gelatin-acid mixture and to denature the collagen matrix within the gelatin precursor is important as some acids are unable to denature bone in accordance with the conditions of the present disclosure or result in undesirable traits. For example, hydrochloric acid (12M), glacial acetic acid (99.7% w/w), and sulfuric acid (1N) each are unable to denature bone in the conditions of the disclosed process. Further, while nitric acid (70% w/w) is capable of denaturing bone in the conditions of the disclosed process, the process results in an odor described as a sewage waste smell and an undesirable yellow-orange coloration to the resulting bone putty.

The phosphoric acid and the gelatin precursor are combined and agitated at a temperature less than 30° C. and then subsequently agitated at a second temperature in excess of 50° C. The two-step agitation of the phosphoric acid and the gelatin precursor achieves the desired denaturation of the gelatin precursor as qualitatively determined based on liquidity and coloration of the gelatin post-neutralization.

In one or more embodiments, the initial agitation at a temperature less than 30° C. includes vortexing the mixture of phosphoric acid and the gelatin precursor at ambient temperature for 1 to 5 minutes. The ambient temperature may be 20° C. to 25° C., for example, and the vortexer may operate at a speed of 2000 to 2500 revolutions per minute (rpm). In a specific embodiment, the mixture of phosphoric acid and the gelatin precursor are vortexed for approximately 3 minutes. The initial agitation exposes all surfaces of the gelatin precursor, such as bone particles, to the phosphoric acid to prevent areas of untreated gelatin precursor during subsequent agitation steps. Without the initial agitation, the denaturation could be uneven. Specifically, it may require at least a half hour to one hour for the bone in the treated steps to denature to an extent which is liquid enough for the acid to permeate untreated areas, and these areas won't be denatured enough at the point of dilution and neutralization to achieve yields without the initial agitation step to exposed all surfaces of the gelatin precursor. If the acid treatment was extended longer, a risk is introduced of over-denatured and the commensurate impact on yields.

The agitation at a second temperature in excess of 50° C. completes the denaturation of the gelatin precursor. In one or more embodiments, the subsequent agitation at a temperature in excess of 55° C. includes agitating the mixture of the gelatin precursor and the phosphoric acid at a temperature of 55° C. to 70° C. for 1 to 4 hours. In further embodiments, the agitation may be completed at a temperature of 55° C. to 65° C., 60° C. to 70° C., 58° C. to 62° C., or approximately 60° C. for 1 to 3 hours, 2 to 4 hours, 1.5 to 2.5 hours, 1.75 to 2.25 hours, or approximately 2 hours. Extended agitation time may result in overly denaturing the gelatin precursor whereas shortening the agitation time may result in an increase in residual salts and insufficient denaturing of the gelatin precursor. Further, agitation at a lesser temperature increases the risk of insufficient denaturing and increases salts in the resulting product.

In one or more embodiments, the agitation at a second temperature in excess of 50° C. may be completed using a rotary shaker. For example, the mixture of the gelatin precursor and the phosphoric acid may be agitated using an orbital shaker with an orbital radius of 19 mm at a speed of 225 to 275 rpm or an orbital radius of 10 mm at a speed of 600 to 650 rpm.

The phosphoric acid in various embodiments may be provided at a concentration of 65 to 99% w/w (mass solute/mass solution×100), 75 to 95% w/w, 80 to 90% w/w, 83 to 87% w/w, or approximately 85% w/w. Any dilution of the phosphoric acid may be achieved with water.

In various embodiments where the gelatin precursor is derived from demineralized human bone, the gelatin precursor is treated with 85% w/w phosphoric acid at a ratio of 0.8 to 2.5 milliliters (ml) per 1 gram of gelatin precursor, 1.0 to 2.2 ml per 1 gram of gelatin precursor, 1.2 to 2.0 ml per 1 gram of gelatin precursor, or 1.4 to 2.8 ml per 1 gram of gelatin precursor. In one or more specific embodiments where the gelatin precursor is derived from demineralized human bone, the gelatin precursor is treated with 85% w/w phosphoric acid at a ratio of approximately 1.6 ml per 1 gram of gelatin precursor. It will be appreciated that the ratio of phosphoric acid to gelatin precursor may vary based on the concentration of the phosphoric acid. Specifically, the desired concentration is influenced by the viscosity of the acid. A more dilute acid would necessitate a reduction in the ratio of phosphoric acid to gelatin precursor, but a longer denaturation time and/or increased denaturation temperature would be required. Conversely, a more concentrated acid would necessitate an increase in the ratio of phosphoric acid to gelatin precursor with less denaturation time and/or a lower denaturation temperature. One skilled in the art is capable of converting the disclosed ratios for differing phosphoric acid concentrations.

Without wishing to be bound by theory, it is believed that decreasing the ratio of acid to gelatin precursor results in a commensurate need for extension of the treatment time required for sufficient denaturation. Conversely, increasing the ratio of acid to gelatin precursor results in greater generation of trisodium phosphate and decreases the treatment time required for sufficient denaturation, thereby potentially resulting in overly denaturing the gelatin precursor.

The gelatin-acid mixture is subsequently neutralized with an alkali to a pH between 6 and 8. Neutralizing the gelatin-acid mixture with the alkali results in separation of a gelatin-rich solution and a waste solution. The gelatin-rich solution comprises the gelatin produced from the gelatin precursor as well as water and sodium phosphates. The waste solution comprises the remaining constituents of the gelatin-acid mixture and the alkali, namely multiple isoforms of sodium phosphates and water. It will be appreciated that the reaction mechanism may be in accordance with Reaction 1.

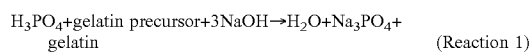

$$H_3PO_4 + \text{gelatin precursor} + 3NaOH \rightarrow H_2O + Na_3PO_4 + \text{gelatin} \quad \text{(Reaction 1)}$$

The gelatin-acid mixture may also be diluted with water prior to introduction of the alkali. Dilution of the gelatin-acid mixture provides ample volume for separation of the gelatin-rich solution and the waste solution. Additionally, dilution of the gelatin-acid mixture before introduction of the alkali reduces the likelihood of a thermoexplosive reaction during the neutralization process. However, excessive dilution may result in a loss of gelatin. In various embodiments, the dilution of the gelatin-acid mixture prior to introduction of the alkali may comprise addition of 4 to 6 ml of water per 1 ml of phosphoric acid, 4.5 to 5.5 ml of water per 1 ml of phosphoric acid, or approximately 5 ml of water per 1 ml of phosphoric acid. In one or more embodiments, the gelatin-acid mixture and the dilution water may be actively mixed during or after addition to ensure homogeneity of the resulting solution before alkali addition.

In one or more embodiments the alkali is sodium hydroxide. The sodium hydroxide in various embodiments may be provided at a concentration of 45 to 55% w/w, 48 to 52% w/w, or approximately 50% w/w when the gelatin-acid mixture was previously diluted at a 5:1 volume to volume (v/v) ratio of water to phosphoric acid. It will be appreciated that the concentration of the alkali added may vary based on the extent of previous dilution of the gelatin-acid mixture. Specifically, if the gelatin-acid mixture was diluted at less than a 5:1 v/v ratio of water to phosphoric acid (4:1 v/v, for example), the concentration of the alkali may be reduced to add additional water. Conversely, if the gelatin-acid mixture was diluted at greater than a 5:1 v/v ratio of water to phosphoric acid (6:1 v/v, for example), the concentration of the alkali may be increased so as to minimize the input of additional water. One skilled in the art is capable of maintaining a water balance by balancing the dilution ratio and the concentration of the alkali.

In various embodiments, sodium hydroxide (as the alkali) may be added at a ratio of 1 to 2 ml of sodium hydroxide per 1 ml of phosphoric acid, 1.1 to 1.6 ml of sodium hydroxide per 1 ml of phosphoric acid, 1.2 to 1.4 ml of sodium hydroxide per 1 ml of phosphoric acid, or approximately 1.3 ml of sodium hydroxide per 1 ml of phosphoric acid. It will be appreciated that the ratio of alkali to phosphoric acid may be selected to reach a resulting pH of 6 to 8 and, as such, the ratio may be adjusted when the alkali is other than 50% w/w sodium hydroxide.

It is noted that calcium hydroxide does not perform well as the alkali. Specifically, when calcium hydroxide is utilized, a rising batter is formed resulting in undesirable properties. Specifically, a dark rising dough-like mass with a moist consistency speckled with white from the calcium hydroxide forms as calcium hydroxide doesn't mix in well.

Further, and the reaction with calcium hydroxide is not easily controlled and is more exothermic than using sodium hydroxide, but slower and less predictable.

The alkali is added to the gelatin-acid mixture at a controlled rate and position. Additionally, during addition of the alkali the resulting solution may be mechanically stirred to maintain homogeneity of the resulting mixture during addition, as addition of an alkali to a static acid solution may result in thermoexplosions. Controlling the rate and position of alkali addition allows the neutralization reaction to proceed in a controlled manner.

Figure 2:
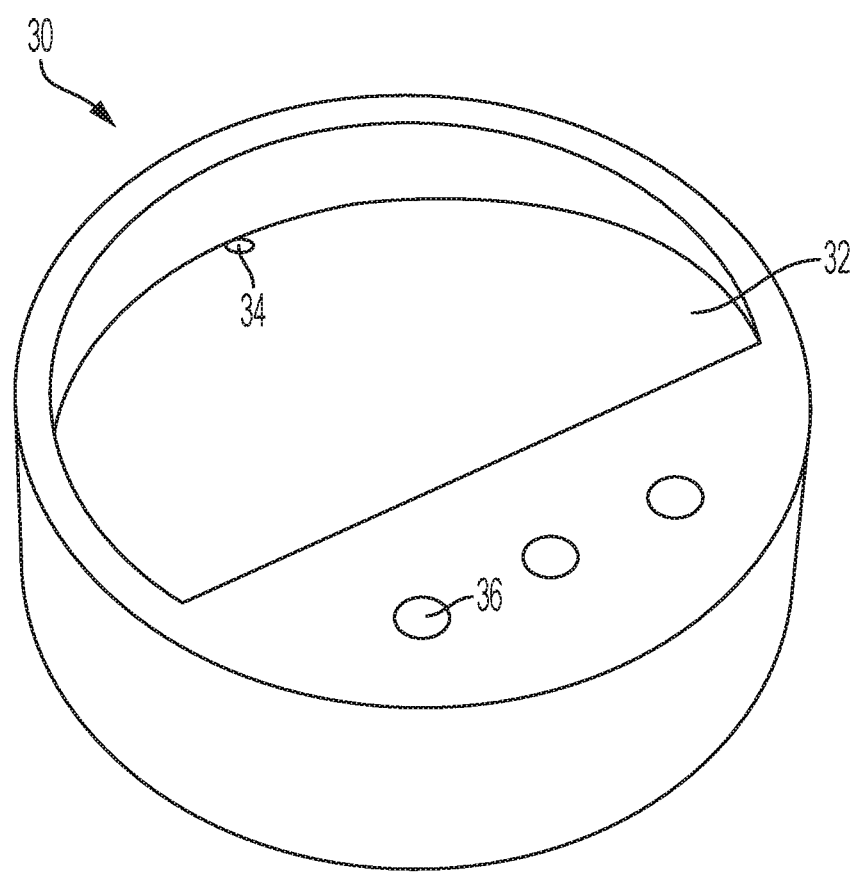
FIG. 2 depicts a distribution lid of the customized reaction vessel of FIG. 1, according to one or more embodiments shown and described herein.

To avoid uncontrolled addition of the alkali to the gelatin-acid mixture the alkali may be added to a metering system which throttles the rate of alkali addition. With reference to FIGS. 1 and 2, in one or more embodiments, the addition of the alkali to the gelatin-acid mixture may be performed with a customized reaction vessel 10. The customized reaction vessel 10 may include a reaction chamber 20 and a distribution lid 30. The distribution lid 30 is configured to naturally add the alkali to the reaction chamber 20 at a controlled rate and position. Specially, the distribution lid 30 includes an alkali reservoir 32 with a sloped base to gravity feed an aqueous alkali solution placed therein toward a drain 34. The drain 34 is placed at the periphery of the distribution lid 30 and the edge of the alkali reservoir 32. With the gelatin-acid mixture in the reaction chamber 20, the distribution lid 30 may be placed on top of the reaction chamber 20 such that the drain 34 aligns with an interior wall 22 of the reaction chamber 20. Subsequently, the alkali may be added to the alkali reservoir 32 to be automatically flowed into the reaction chamber 20 via the drain 34 in a controlled manner. The drain 34 is sized to allow a safe flow rate of alkali addition based on principles of fluid mechanics known to one skilled in the art and the drain 34 is positioned such that the alkali flows down the interior wall 22 of the reaction chamber 20. It will further be appreciated that the distribution lid may further include vents 36 to allow air and/or heat from the interior of the reaction chamber 20 to escape during the neutralization process.

The gelatin-rich solution and the waste solution are separated to allow further processing of the gelatin-rich solution. The gelatin-rich solution and the waste solution naturally separate into layers upon neutralization of the gelatin-acid mixture when statically held. The gelatin-rich solution naturally positions on top of the waste solution based on differing densities. In one or more embodiments, the gelatin-rich solution may be scooped away from the waste solution for further processing. In further embodiments, the customized reaction vessel 10 may be utilized to drain away the waste solution. Specifically, the customized reaction vessel 10 may include a waste outlet 40 proximal the bottom of the reaction chamber 20. The waste outlet 40 allows the waste solution to be controllably drained from the reaction chamber 20 such that the gelatin-rich solution and a minimal amount of waste solution remains in the reaction chamber 20. The waste outlet 40 may comprise a ball valve, clamped hose, or any other mechanism to control and throttle flow out of the reaction chamber 20.

Residual salts are removed from the gelatin-rich solution to obtain purified gelatin. The residual salts include a majority trisodium phosphate along with disodium phosphate and monosodium phosphate and trace amounts of calcium phosphates. In one or more embodiments, removing residual salts from the gelatin-rich solution comprises centrifugation of the gelatin-rich solution against a filtration media at 450 to 1000 times standard gravity. In various embodiments, the centrifugation achieves a force of 500 to 900 times standard gravity, 600 to 800 times standard gravity, 650 to 750 times standard gravity, or approximately 700 times standard gravity. It will be appreciated that a slower centrifugation speed results in less force applied and a commensurate reduction in residual salt and waste removal from the gelatin-rich solution.

In one or more embodiments, the centrifugation to remove the residual salts from the gelatin-rich solution is achieved with at least two separate centrifugation steps separated by an intermediate heating of the gelatin-rich solution. Specifically, removing residual salts from the gelatin-rich solution may comprise an initial separation with primary centrifugation against a filtration media at 450 to 1000 times standard gravity for at least 2 minutes. In various embodiments, the primary centrifugation may be continued for 2 to 8 minutes, 3 to 7 minutes, 4 to 6 minutes, or approximately 5 minutes. Subsequently, the residual gelatin-rich solution may be heated to a temperature of 55° C. to 65° C. under static conditions for 5 to 30 minutes. In various embodiments, the heating may be to 57° C. to 63° C., 58° C. to 62° C., or approximately 60° C. for 10 to 30 minutes, 15 to 25 minutes, 18 to 22 minutes, or approximately 20 minutes. Finally, additional residual salts are removed from the gelatin-rich solution with an additional separation by secondary centrifugation against the filtration media at 450 to 1000 times standard gravity for at least 2 minutes. In various embodiments, the secondary centrifugation may be continued for 2 to 8 minutes, 3 to 7 minutes, 4 to 6 minutes, or approximately 5 minutes. While specific exerted forces of 450 to 1000 times standard gravity are discussed for the primary and secondary centrifugation, it will be further appreciated that the exerted force may also fall within the ranges previously discussed of 500 to 900 times standard gravity, 600 to 800 times standard gravity, 650 to 750 times standard gravity, or approximately 700 times standard gravity.

Figure 3:
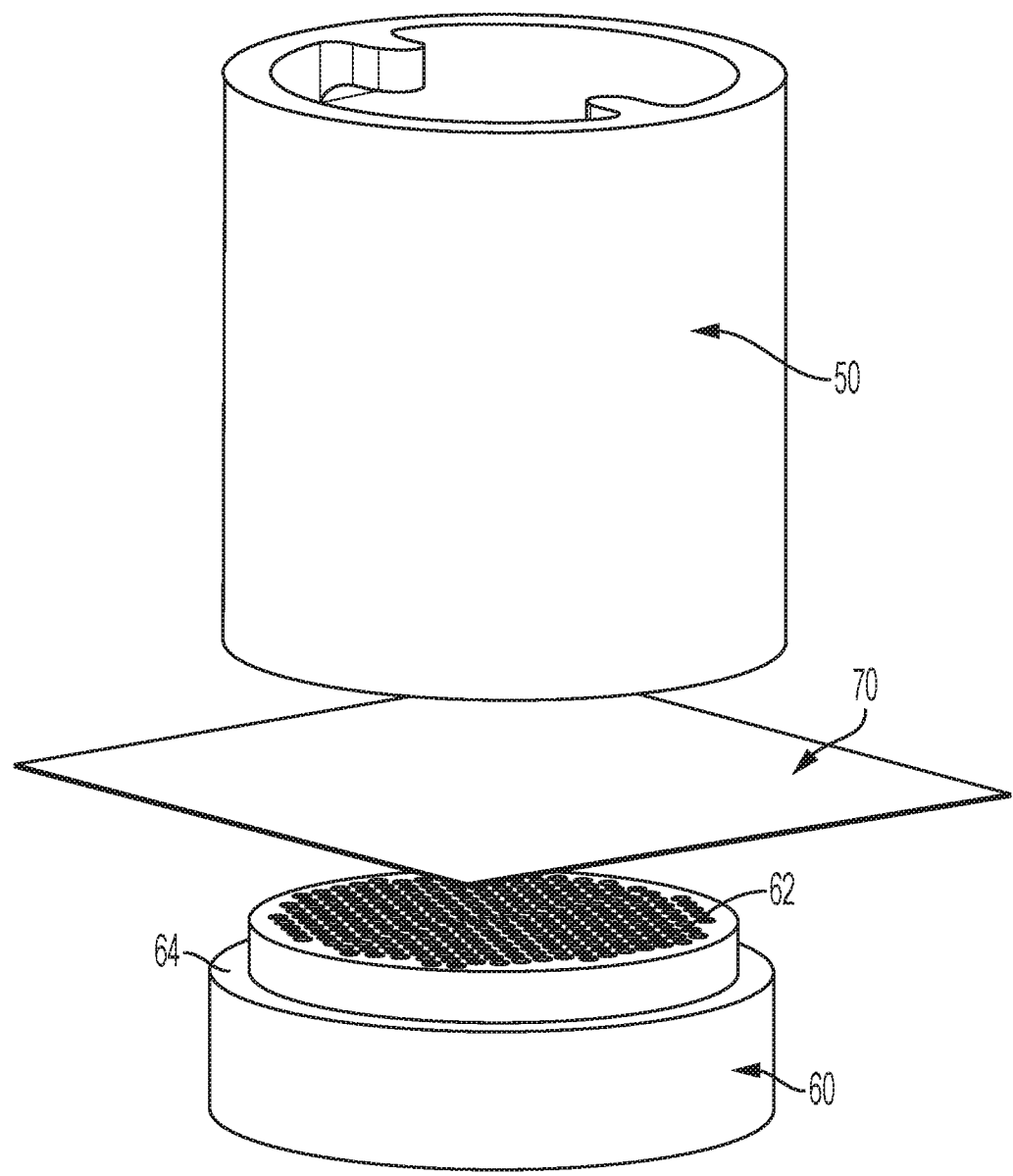
FIG. 3 depicts a residual salt and waste removal system, according to one or more embodiments shown and described herein.

With reference to FIG. 3, the centrifugation of the gelatin-rich solution may be performed with a specialized waste removal centrifuge cup 50 and grate 60 of a residual salt and waste removal system. Specifically, the grate 60 and the waste removal centrifuge cup 50 are placed in a standard centrifuge cup with the filtration media 70 placed between the grate 60 and the waste removal centrifuge cup 50. The grate 60 comprises a plurality of drainage channels 62 to allow fluid to pass through and into the standard centrifuge cup during centrifugation. The grate 60 additionally comprises a flange 64 having a reduced diameter sized to interface with an open bottom of the waste removal centrifuge cup 50, thereby trapping the filtration media 70 therebetween in a fluid tight configuration. The gelatin-rich solution is placed in the waste removal centrifuge cup 50 and during active centrifugation the increased gravitational force results in passage of fluid and the dissolved residual salts through the filtration media 70, through the grate 60 via drainage channels 62, and into the standard centrifuge cup. The purified gelatin is retained in the waste removal centrifuge cup 50 by the filtration media 70 for further processing.

The filtration media may comprise any planar material which allows passage of fluids but not gelatin. In one or more embodiments, the filtration media is a sheet of flashspun high-density polyethylene fibers, such as commercially available Tyvek from DuPont (Midland, Mich.). In various further embodiments, the filtration media may alternatively comprise ultra-fine metal mesh such as Stainless Steel; open cell polyurethane or PVC based foams; filtering medium comprised of polymers such as polypropylene, copolymer, polytetrafluoroethylene, polyethylene, and/or nylon; or woven filtering fabrics made of nylon, polyester, rayon, acrylics, glass fibers. Selection of filtration media is completed with consideration of selection of a material that allows for the passage of water, salts (trisodium phosphate) and other waste constituents, but does not allow passage of the gelatin rich solution as well as being free of adverse reaction with the waste streams and the gelatin rich solution.

In one or more embodiments, the residual salts may be removed from the gelatin-rich solution by placing the gelatin-rich solution in the filtration media and manually wringing remaining fluid and dissolved residual salts from the gelatin-rich solution to obtain purified gelatin.

The purified gelatin obtained by removing residual salts from the gelatin-rich solution is subsequently dried. Various methods of drying the purified gelatin include freeze drying, vacuum drying, or other known methods absent of heating. In various embodiments, the purified gelatin is dried to a moisture level of less than 10%, less than 8%, or less than 6% by weight. If the moisture in the dried purified gelatin is too great, the gelatin particulates may melt causing the final reconstitutable implantable bone putty to become sticky and lack performance.

In one or more embodiments, drying the purified gelatin comprises morselizing the purified gelatin followed by application of a freeze drying process to remove moisture from the purified gelatin. Freeze drying parameters would be known to one skilled in the art based on the size of the morselized gelatin and the residual moisture levels. Morselizing the purified gelatin may be achieved through any method to break the bulk purified gelatin into smaller sections with an increased surface area, thereby allowing for greater moisture removal. Example methods of morselizing include passage through a bone mill, a garlic cuber, a planar mill in the style of a cheese grater, or breaking apart by hand.

The dried purified gelatin is finally reduced to particulates having a largest dimension less than 300 micrometers (μm) to generate the gelatin particulates. In various embodiments, the gelatin particulates have a largest dimension of less than 275 μm, less than 250 μm, less than 225 μm, or less than 200 μm.

The dried purified gelatin may be reduced to the gelatin particulates by milling through a 0.2 mm gapless screen. In one or more embodiments, the mill may be a rotary mill such as those commercially available from Retsch (Haan, Germany) and may be operated at 8000 or less rpm, 6000 or less rpm, or 4000 or less rpm with a rotor diameter of 99 mm. Excessive milling speed may result in melting of the purified gelatin during the milling operation.

The reconstitutable implantable bone putty may be formed by combining the previously discussed bone matrix derived from human bone and gelatin particulates at a concentration of the bone matrix by dry weight of 20 to 60 percent. The reconstitutable implantable bone putty may be provided in a dry particulate form to be reconstituted by medical staff at the time of implantation or may be provided in a ready-to-use putty form with reconstitution completed prior to final packaging. In various embodiments of the dry particulate form, the bone matrix and gelatin particulates may be combined at a concentration of the bone matrix by dry weight of 20 to 50 percent, 25 to 45 percent, 30 to 40 percent, or approximately 35 percent. In various embodiments of the ready-to-use putty form, the bone matrix and gelatin particulates may be combined at a concentration of the bone matrix by dry weight of 24 to 60 percent, 30 to 54 percent, 36 to 48 percent, or approximately 42 percent.

Combining the bone matrix and the gelatin particulates may be achieved with any mixing method known to those skilled in the art. In one or more embodiments, the bone matrix and the gelatin particulates are combined by vortexing for 1 to 5 minutes until a uniform distribution of the bone matrix and the gelatin particulates is obtained.

An implantable bone putty may be formed from the reconstitutable implantable bone putty. Methods of preparing the implantable bone putty include preparing the reconstitutable implantable bone putty in accordance with the present disclosure and adding a reconstitution media. The reconstitutable implantable bone putty and the reconstitution media may be combined with any mixing method known to those skilled in the art. In one or more embodiments, the reconstitutable implantable bone putty and the reconstitution media are combined by vortexing for 1 to 5 minutes until a uniform distribution of the bone matrix and the gelatin particulates is obtained. In various embodiments, the reconstitution media may comprise one or more of water, saline, blood, plasma, interstitial fluid, fat, cellular medium, or amniotic fluid.

In one or more embodiments, the implantable bone putty comprises the reconstitution media at a ratio of 1 to 3 milliliters of reconstitution media per gram of gelatin particulate. As previously discussed, the reconstitutable implantable bone putty may be provided in a dry particulate form to be reconstituted by medical staff at the time of implantation or may be provided in a ready-to-use putty form with reconstitution completed prior to final packaging. The ratio of reconstitution media per gram of gelatin particulate may differ for reconstitution of the dry particulate form and the ready-to-use putty form. In various embodiments of the dry particulate form, the reconstitutable implantable bone putty may be reconstituted with the reconstitution media at a ratio of 1 to 2.5 milliliters, 1 to 2 milliliters, 1 to 1.5 milliliters, or approximately 1.2 milliliters of reconstitution media per gram of gelatin particulate. The dry format provides an option for customization at the point of care by the clinician with the ability to add more or less reconstitution media to match properties desired by the clinician based on their expertise in treating patients. For example, the clinician may desire differing properties of the bone putty based on patient specific criterion. In various embodiments of the ready-to-use putty form, the reconstitutable implantable bone putty may be reconstituted with the reconstitution media at a ratio of 1.5 to 3 milliliters, 1.5 to 2.5 milliliters, 1.75 to 2.25 milliliters, or approximately 1.9 milliliters of reconstitution media per gram of gelatin particulate.

Having described the methods of preparing a reconstitutable implantable bone putty and preparing an implantable bone putty therefrom, it will be appreciated that the formed reconstitutable implantable bone putty is also described by the present disclosure. The formed reconstitutable implantable bone putty or implantable bone putty may be packed into an air tight container. The packaged reconstitutable implantable bone putty may be in the dry particulate form for reconstitution with reconstitution media at the time of use or may be in the ready-to-use putty form for immediate utilization without requiring addition of the reconstitution media. It will be appreciated that that packaged reconstitutable implantable bone putty does not comprise viable cells and therefore is shelf-stable without requiring storage in cold conditions.

In one or more embodiments, additional active agents may be added to the reconstitutable implantable bone putty along with the reconstitution media. Examples of active agents include antimicrobials, anesthetics, and analgesics. The dry particulate form of the reconstitutable implantable bone putty allows the clinician to add appropriate patient specific dosing of desired active agents at the time of reconstitution.

The reconstitutable implantable bone putty demonstrates general biocompatibility in accordance with ISO 10993. Specifically, the reconstitutable implantable bone putty has been demonstrated in accordance with ISO 10993 as non-cytotoxic, non-pyrogenetic, non-genotoxic (non-clastogenic and non-mutagenic), non-sensitizing, and non-irritating as part of testing protocols.

It will be appreciated that the purified gelatin forming the carrier of the reconstitutable implantable bone putty is inert. Specifically, the purified gelatin comprises no bioactive agents or viable cells. However, osteoinductive growth factors and other bioactive agents may be introduced into the reconstitutable implantable bone putty via the bone matrix and/or the reconstitution media.

It should be understood that the various aspects of reconstitutable implantable bone putty, the method of preparing the reconstitutable implantable bone putty, and the method of preparing the implantable bone putty are described and such aspects may be utilized in conjunction with various other aspects.

In a first aspect, the disclosure provides a method of preparing a reconstitutable implantable bone putty. The method comprises the steps of supplying a bone matrix derived from human bone, preparing gelatin particulates derived from human tissue, and combining the bone matrix and the gelatin particulates at a concentration of the bone matrix by dry weight of 20 to 60 percent to form the reconstitutable implantable bone putty. Preparing the gelatin particulates comprises the steps of supplying a gelatin precursor comprising bone or soft tissue from a human, treating the gelatin precursor with phosphoric acid to generate a gelatin-acid mixture, neutralizing the gelatin-acid mixture with an alkali introduced to the gelatin-acid mixture at a controlled rate and position to a pH between 6 and 8 to allow a gelatin-rich solution and a waste solution to separate, removing residual salts from the gelatin-rich solution to obtain purified gelatin, drying the purified gelatin, and reducing the purified gelatin to particulates having a largest dimension less than 300 µm to generate the gelatin particulates. Further, treating the gelatin precursor with phosphoric acid comprises agitation of the gelatin precursor and phosphoric acid at a temperature less than 30° C. prior to agitation at a temperature in excess of 50° C.

In a second aspect, the disclosure provides the method of the first aspect, in which the bone matrix is a demineralized bone matrix.

In a third aspect, the disclosure provides the method of the first aspect, in which the demineralized bone matrix is derived from human cortical bone.

In a fourth aspect, the disclosure provides the method of any of the first through third aspects, in which the bone matrix is provided as particulates sized to less than 800 m In a fifth aspect, the disclosure provides the method of any of the first through fourth aspects, in which the gelatin particulates are derived from human bone.

In a sixth aspect, the disclosure provides the method of any of the first through fifth aspects, in which the gelatin particulates are derived from demineralized human cortical bone.

In a seventh aspect, the disclosure provides the method of the fifth or sixth aspects, in which the gelatin precursor is treated with the phosphoric acid at a ratio of 0.8 to 2.5 ml 85% w/w phosphoric acid per 1 gram of gelatin precursor.

In an eighth aspect, the disclosure provides the method of any of the first through seventh aspects, in which agitation of the gelatin precursor and phosphoric acid at a temperature less than 30° C. comprises agitation of the gelatin precursor and phosphoric acid at an ambient temperature of 20° C. to 25° C. for 1 to 5 minutes.

In a ninth aspect, the disclosure provides the method of any of the first through eighth aspects, in which agitation at a temperature in excess of 50° C. comprises agitation at a temperature of 55° C. to 70° C. for 1 to 4 hours.

In a tenth aspect, the disclosure provides the method of any of the first through ninth aspects, in which neutralizing the gelatin-acid mixture with an alkali further comprises diluting the phosphoric acid with water at a ratio of 4 to 6 ml of water per 1 ml of phosphoric acid prior to introduction of the alkali.

In an eleventh aspect, the disclosure provides the method of any of the first through tenth aspects, in which the alkali is 45 to 55% w/w sodium hydroxide.

In a twelfth aspect, the disclosure provides the method of any of the first through eleventh aspects, in which removing residual salts from the gelatin-rich solution comprises centrifugation of the gelatin-rich solution against a filtration media at 450 to 1000 times standard gravity.

In a thirteenth aspect, the disclosure provides the method of the twelfth aspect, in which removing residual salts from the gelatin-rich solution further comprises heating the gelatin-rich solution to 55 to 65° C. for 5 to 30 minutes followed by a second centrifugation of the gelatin-rich solution against the filtration media at 450 to 1000 times standard gravity to separate the residual salts and the purified gelatin.

In a fourteenth aspect, the disclosure provides the method of any of the first through thirteenth aspects, in which drying the purified gelatin comprises morselizing the purified gelatin followed by application of a freeze drying process to remove moisture from the purified gelatin.

In a fifteenth aspect, the disclosure provides a method of preparing an implantable bone putty. The method comprises preparing a reconstitutable implantable bone putty in accordance with any of the first through fourteenth aspects and adding a reconstitution media to the reconstitutable implantable bone putty. The reconstitution media is selected from the group consisting of water, saline, blood, plasma, interstitial fluid, fat, cellular medium, or amniotic fluid.

In a sixteenth aspect, the disclosure provides the method of the fifteenth aspect, in which the implantable bone putty comprises the reconstitution media at a ratio of 1 to 3 milliliters of reconstitution media per gram of gelatin particulate.

In a seventeenth aspect, the disclosure provides a reconstitutable implantable bone putty. The reconstitutable implantable bone putty comprises a bone matrix derived from human bone and gelatin derived from human tissue. The bone matrix is present in the bone putty at a concentration by dry weight of 20 to 60 percent and the gelatin is provided in a dried form consisting of grains sized to less than 300 µm.

In an eighteenth aspect, the disclosure provides the reconstitutable implantable bone putty of the seventeenth aspect, in which the bone matrix is a demineralized bone matrix.

In a nineteenth aspect, the disclosure provides the reconstitutable implantable bone putty of the seventeenth aspect, in which the demineralized bone matrix is derived from human cortical bone.

In a twentieth aspect, the disclosure provides the reconstitutable implantable bone putty of any of the seventeenth through nineteenth aspects, in which the bone matrix consists of particulates sized to less than 800 μm.

In a twenty-first aspect, the disclosure provides the reconstitutable implantable bone putty of any of the seventeenth through twentieth aspects, in which the gelatin is derived from human bone.

In a twenty-second aspect, the disclosure provides the reconstitutable implantable bone putty of any of the seventeenth through twenty-first aspects, in which the gelatin is derived from human cortical bone.

In a twenty-third aspect, the disclosure provides the reconstitutable implantable bone putty of any of the seventeenth through twenty-second aspects, in which the reconstitutable implantable bone putty is entirely derived from demineralized bone matrix.

In a twenty-fourth aspect, the disclosure provides the reconstitutable implantable bone putty of any of the seventeenth through twenty-third aspects, in which the reconstitutable implantable bone putty further comprises a reconstitution media, said reconstitution media selected from the group consisting of water, saline, blood, plasma, interstitial fluid, fat, cellular medium, or amniotic fluid.

In a twenty-fifth aspect, the disclosure provides the reconstitutable implantable bone putty of the twenty-fourth aspect, in which the reconstitutable implantable bone putty comprises the reconstitution media at a ratio of 1 to 3 milliliters of reconstitution media per gram of gelatin.

In a twenty-sixth aspect, the disclosure provides the reconstitutable implantable bone putty of the twenty-fourth or twenty-fifth aspects, in which the reconstitutable implantable bone putty is packaged into an air tight vessel.

It is noted that there is an inherent degree of uncertainty that may be attributed to any quantitative comparison, value, measurement, or other representation. Further it is understood that there is a degree by which a quantitative representation may vary from a stated reference without resulting in a change in the basic function of the subject matter at issue. For conciseness, the terms "about", "substantially" and the like are omit from disclosed values, measurements, or other representations, but are implicitly include within the intended meaning and scope to cover these stated situations.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

It will further be appreciated that the reconstitutable implantable bone putty, the methods of preparing the same, and use of the same are applicable to utilization in any vertebrate species. However, as human use is the principal application of the reconstitutable implantable bone putty detailed within the present disclosure, the description focuses on applying the same in human applications.

What is claimed is:

1. A method of preparing a reconstitutable implantable bone putty, the method comprising:
   supplying a bone matrix derived from human bone;
   preparing gelatin particulates derived from human tissue; and
   combining the bone matrix and the gelatin particulates at a concentration of the bone matrix by dry weight of 20 to 60 percent to form the reconstitutable implantable bone putty,
   wherein preparing the gelatin particulates comprises:
      supplying a gelatin precursor comprising bone or soft tissue from a human;
      treating the gelatin precursor with phosphoric acid to generate a gelatin-acid mixture, wherein treating the gelatin precursor with phosphoric acid comprises agitation of the gelatin precursor and phosphoric acid at a temperature less than 30° C. prior to agitation at a temperature in excess of 50° C.;
      neutralizing the gelatin-acid mixture with an alkali to a pH between 6 and 8, thereby allowing a gelatin-rich solution and a waste solution to separate, wherein the alkali is introduced to the gelatin-acid mixture at a controlled rate and position;
      removing residual salts from the gelatin-rich solution to obtain purified gelatin;
      drying the purified gelatin; and
      reducing the purified gelatin to particulates having a largest dimension less than 300 μm to generate the gelatin particulates.

2. The method of claim 1, wherein the bone matrix is a demineralized bone matrix.

3. The method of claim 2, wherein the demineralized bone matrix is derived from human cortical bone.

4. The method of claim 1, wherein the bone matrix is provided as particulates sized to less than 800 μm.

5. The method of claim 1, wherein the gelatin particulates are derived from human bone.

6. The method of claim 5, wherein the gelatin particulates are derived from demineralized human cortical bone.

7. The method of claim 5, wherein the gelatin precursor is treated with the phosphoric acid at a ratio of 0.8 to 2.5 ml 85% w/w phosphoric acid per 1 gram of gelatin precursor.

8. The method of claim 1, wherein agitation of the gelatin precursor and phosphoric acid at a temperature less than 30° C. comprises agitation of the gelatin precursor and phosphoric acid at an ambient temperature of 20° C. to 25° C. for 1 to 5 minutes.

9. The method of claim 1, wherein agitation at a temperature in excess of 50° C. comprises agitation at a temperature of 55° C. to 70° C. for 1 to 4 hours.

10. The method of claim 1, wherein neutralizing the gelatin-acid mixture with an alkali further comprises diluting the phosphoric acid with water at a ratio of 4 to 6 ml of water per 1 ml of phosphoric acid prior to introduction of the alkali.

11. The method of claim 1, wherein the alkali is 45 to 55% w/w sodium hydroxide.

12. The method of claim 1, wherein removing residual salts from the gelatin-rich solution comprises centrifugation of the gelatin-rich solution against a filtration media at 450 to 1000 times standard gravity.

13. The method of claim 12, wherein removing residual salts from the gelatin-rich solution further comprises heating the gelatin-rich solution to 55 to 65° C. for 5 to 30 minutes followed by a second centrifugation of the gelatin-rich solution against the filtration media at 450 to 1000 times standard gravity to separate the residual salts and the purified gelatin.

14. A method of preparing an implantable bone putty, the method comprising:
   preparing a reconstitutable implantable bone putty in accordance with claim 1; and
   adding a reconstitution media to the reconstitutable implantable bone putty, said reconstitution media selected from the group consisting of water, saline, blood, plasma, interstitial fluid, fat, cellular medium, or amniotic fluid.

15. The method of claim 14, wherein the implantable bone putty comprises the reconstitution media at a ratio of 1 to 3 milliliters of reconstitution media per gram of gelatin particulate.

* * * * *